United States Patent [19]

Tararuj et al.

[11] Patent Number: 5,611,972
[45] Date of Patent: Mar. 18, 1997

[54] DEVICES AND RELATED METHOD FOR THE SELECTIVE EXPOSURE OF MICROENCAPSULATED LIQUIDS

[75] Inventors: Christopher Tararuj, Hamilton; Hung Y. Chao, Princeton Junction, both of N.J.

[73] Assignee: Webcraft Technologies, Inc., Horsham, Pa.

[21] Appl. No.: 647,257

[22] Filed: May 13, 1996

Related U.S. Application Data

[63] Continuation of Ser. No. 227,262, Apr. 13, 1994, abandoned.

[51] Int. Cl.$^6$ .................. B01J 13/02; B01J 13/04
[52] U.S. Cl. ................ 264/4.1; 428/201; 424/401
[58] Field of Search .................. 264/4.1; 428/201; 424/401

[56] References Cited

U.S. PATENT DOCUMENTS

| | | | |
|---|---|---|---|
| 3,516,846 | 6/1970 | Matson | 428/313.5 |
| 3,516,941 | 6/1970 | Matson | 428/313.5 |
| 3,691,140 | 9/1972 | Silver | 524/153 |
| 3,778,383 | 12/1973 | Schibler et al. | 252/316 |
| 4,087,376 | 5/1978 | Foris et al. | 252/316 |
| 4,089,802 | 5/1978 | Foris et al. | 252/316 |
| 4,100,103 | 7/1978 | Foris et al. | 252/316 |
| 4,166,152 | 8/1979 | Baker et al. | 428/527 |
| 4,209,188 | 6/1980 | Chao et al. | 282/27.5 |
| 4,251,386 | 2/1981 | Saeki et al. | 424/32 |
| 4,487,801 | 12/1984 | Turnbull et al. | 428/313.5 |
| 4,495,509 | 1/1985 | Chao | 346/215 |
| 4,599,271 | 7/1986 | Chao | 428/402.21 |
| 4,626,471 | 12/1986 | Chao | 428/402.21 |
| 4,720,417 | 1/1988 | Sweeney et al. | 428/20 |
| 4,785,048 | 11/1988 | Chao | 524/745 |
| 4,925,517 | 5/1990 | Charbonneau et al. | 156/276 |
| 4,988,557 | 1/1991 | Charbonneau | 428/204 |
| 5,015,527 | 5/1991 | Chao | 428/402.21 |
| 5,314,944 | 5/1994 | Chao | 534/501 |
| 5,352,648 | 10/1994 | Chao | 503/206 |

FOREIGN PATENT DOCUMENTS

| | | |
|---|---|---|
| 1156725 | 7/1964 | United Kingdom . |
| 2041319 | 11/1979 | United Kingdom . |
| 2048206 | 3/1980 | United Kingdom . |
| WO94/12072 | 6/1994 | WIPO . |

*Primary Examiner*—Nathan M. Nutter
*Attorney, Agent, or Firm*—Leydig, Voit & Mayer, Ltd.

[57] ABSTRACT

A reusable device for exposing a microencapsulated liquid, e.g., a fragrance, comprising two surfaces adhered to each other by an adhesive composition, the adhesive composition comprising a non-film forming adhesive comprising a plurality of adhesive polymeric microparticles and microcapsules of an average diameter of about 5 µm to about 60 µm which have the liquid therein and which are adhered to each surface by the adhesive, wherein at least a portion of the microcapsules are broken when the surfaces are separated, and wherein the adhesive has the ability to readhere the surfaces to each other after the surfaces are separated and microcapsules broken. A method providing for the repeated, selective exposure of a microencapsulated liquid using the aforesaid device is also provided.

13 Claims, No Drawings

DEVICES AND RELATED METHOD FOR THE SELECTIVE EXPOSURE OF MICROENCAPSULATED LIQUIDS

This is a continuation of application Ser. No. 08/227,262 filed on Apr. 13, 1994 and now abandoned.

TECHNICAL FIELD OF THE INVENTION

The present invention relates to devices containing microcapsules which can be ruptured to release a material encapsulated therein and related methods for their use. More specifically, the invention relates to microcapsules that are secured between two temporarily adhered surfaces such that upon separation of such surfaces, the microcapsules rupture and release a liquid, e.g., a fragrant liquid, contained therein.

BACKGROUND OF THE INVENTION

Rupturable microcapsules, i.e., generally spherical shells which are designed to be broken such that material encapsulated therein is exposed to the surrounding environment, have been used for many years in a wide variety of commercial applications. These applications have ranged from using such microcapsules as image sources on a recording medium to their use as sources of fragrant liquid in perfume and cologne samplers.

A wide variety of methods exist by which such rupturable microcapsules can be manufactured, all of these methods being well known to those skilled in the art. These processes may be conveniently segregated, as will be appreciated by those skilled in the art, into several groups based upon the chemistry used in forming the microcapsule: gelatin systems, melamine-formaldehyde systems, urea-formaldehyde systems, polyamide systems, and polyurea systems. Examples of such processes are provided by U.S. Pat. Nos. 3,516,846; 3,516,941; 3,778,383; 4,087,376; 4,089,802; 4,100,103; and 4,251,386, as well as by U.K Patents 1,156,725; 2,041,319; and 2,048,206.

One commercially significant application of the aforesaid methods is in the microencapsulation of fragrant liquids, such as perfumes and colognes, such being necessary in the preparation of fragrance samplers. Samplers of this type are typically inserted into magazines, or handed out individually by salespersons at retail establishments, to promote the sale of the perfume or cologne contained therein. These samplers generally comprise two sheets of material, e.g., paper, which are temporarily bonded to each other by means of a film-forming adhesive which has rupturable microcapsules dispersed therein. This adhesive further bonds the individual microcapsules to both sheets of the material. Thus, when the sheets are separated, the microcapsules will rupture, thereby releasing the fragrant liquid.

One well-recognized and long-standing problem associated with these samplers is that, once such samplers are opened and the fragrance released, there is no suitable means for the user to avoid further exposure to the liquid other than by discarding the sampler. This has been recognized as being of particular concern in respect to fragrance samplers.

In addition, such samplers are constructed in manner which allows them to be effectively used only once. Thus, the same or another user is prevented, from a practical standpoint, from re-sampling the encapsulated liquid at a later time determined by the user, i.e., selective re-sampling.

Thus, there exists a need for a device and related method which would allow a user to sample a microencapsulated liquid and, after said sampling is completed, to avoid, or at least partially avoid, further detection of the liquid by the user. Moreover, a device and related method are needed which would allow one to selectively re-sample the liquid using the same device. The present invention seeks to satisfy those needs.

These and other advantages of the present invention, as well as additional inventive features, will be apparent from the description of the invention provided herein.

SUMMARY OF THE INVENTION

The present invention provides a reusable device for exposing a microencapsulated liquid comprising two surfaces adhered to each other by an adhesive composition, the adhesive composition comprising a non-film forming adhesive comprising a plurality of adhesive polymeric microparticles and microcapsules of an average diameter of about 5 μm to about 60 μm which have the liquid therein and which are adhered to each surface by the adhesive, wherein at least a portion of the microcapsules are broken when the surfaces are separated, and wherein the adhesive has the ability to readhere the surfaces to each other after the surfaces are separated and microcapsules broken.

A method which provides for repeated, selective exposure of a microencapsulated liquid is also contemplated by the present invention. The method comprises (a) providing two surfaces adhered to each other by an adhesive composition, the adhesive composition comprising a non-film forming adhesive comprising a plurality of adhesive polymeric microparticles and microcapsules of an average diameter of about 5 μm to about 60 μm which have the liquid therein, wherein at least a portion of the microcapsules are broken when the surfaces are separated, and wherein the adhesive has the ability to readhere the surfaces to each other after the surfaces are separated and microcapsules broken, (b) separating the two surfaces to break the at least a portion of the microcapsules, and (c) contacting the two surfaces to readhere the two surfaces to each other.

DESCRIPTION OF THE PREFERRED EMBODIMENTS

The present invention provides a device and related method for exposing a microencapsulated liquid. The device and related method are unique in the manner in which they allow a user to sample a microencapsulated liquid and, after said sampling is completed, to avoid, or at least partially avoid, further detection of the liquid by the user. The device and method further allow one to selectively, i.e., at a time determined by the user, re-sample the liquid. Thus, the present invention allows a user to exert at least partial control over the period of time the liquid is able to be detected by the user.

One embodiment of the present invention includes a reusable device for exposing a microencapsulated liquid comprising two surfaces adhered to each other by an adhesive composition, the adhesive composition comprising a non-film forming adhesive comprising a plurality of adhesive polymeric microparticles and microcapsules of an average diameter of about 5 μm to about 60 μm which have the liquid therein and which are adhered to each surface by the adhesive, wherein at least a portion of the microcapsules are broken when the surfaces are separated, and wherein the adhesive has the ability to readhere the surfaces to each other after the surfaces are separated and microcapsules broken.

The adhesive used in the present invention is a non-film-forming adhesive comprising a plurality of adhesive polymeric microparticles. These adhesive microparticles, which are generally spherical in nature, are well known in the art, but it is believed that such have not previously been used in connection with microcapsules in the manner of the present invention.

Such adhesives function in a manner which is unique as compared to conventional film-forming adhesives. Conventional film-forming adhesives used in samplers to bond the two surfaces together, and microcapsules thereto, retain little or no adhesiveness after the sampler is opened. Thus, samplers constructed in this manner may be used only once, and provide no means by which the liquid exposed by that one opening can be controlled.

In contrast, the polymeric non-film-forming microparticulate adhesives used to adhere the two surfaces and microcapsules in the manner of the present invention will stretch for a period of time as the surfaces are separated and, at a certain point, snap back into their original configuration, while retaining their adhesive properties.

These microparticles, when used in the manner of the present invention, possess certain adhesive characteristics which enable at least a portion of the microcapsules to be broken, while another portion of the microcapsules remain intact. In addition, such microparticles possess the ability to readhere the surfaces to each other after the surfaces are separated and microcapsules broken over several cycles.

The use of such an adhesive in the present inventive device allows for the re-sealing of the device after sampling has occurred, i.e., the microparticulate adhesive provides for the re-adhesion of the sheets to each other, thereby covering the ruptured microcapsules and the liquid remaining within the ruptured microcapsules, as well as the liquid residing on the adhesive or on a surface. Such, in turn, allows one to avoid, or at least partially avoid, further exposure to the liquid.

A further characteristic of the present invention, which is due in large part to the use of the non-film-forming adhesive as described herein, is that substantially all of the microcapsules are not broken when the surfaces are separated, as is generally the case when a film-forming adhesive is used. Instead, only a first portion of the microcapsules are broken after the surfaces are separated, with a second portion of the microcapsules remaining unbroken. All, or more likely a portion, of the unbroken microcapsules which constitute the second portion, may subsequently become adhered to each sheet upon said re-sealing and, therefore, broken upon the subsequent re-sampling of the device. This phenomenon will be repeated during subsequent uses, advantageously providing for at least a portion of the microcapsules to be broken during each sampling. This allows each sampling of the encapsulated liquid to comprise, at least in part, newly released liquid, providing for a relatively consistent sampling even during re-use of the device.

The adhesive microparticles may be advantageously formed from at least one alkyl acrylate polymer (this term including copolymers thereof). When such are used, it is preferable that the alkyl groups thereof contain from 4–12 carbon atoms and, more preferably, from 8–12 carbon atoms. When the adhesives contain the aforesaid levels of carbon atoms, a level of adhesion appropriate for purposes of the present invention is obtained. If too low a level of carbon atoms is present, the microparticles are too hard, rendering them insufficiently adherent for use in connection with the present invention. Conversely, when excessive carbon atoms are present, the microparticles are too soft and sticky, resulting in the undesirable formation of particle agglomerations. The adhesive tensile strength of such suitable adhesives may advantageously range from about 10 to about 80 g/cm, as measured using an Instron Tensile Tester.

Exemplary of the aforedescribed most preferred adhesives are those selected from the group consisting of poly(isooctyl acrylate), poly(2-ethylhexyl acrylate), and mixtures thereof. Further descriptions of those adhesives are provided in U.S. Pat. Nos. 3,691,140 and 4,166,152.

The microcapsules used in the present invention have an average diameter of about 5 µm to about 60 µm and a material, such as a liquid, encapsulated therein. While the liquid may be any liquid which is able to be encapsulated, one commercially significant use of the present invention is in connection with liquids which emit an odor, e.g., colognes and perfumes. However, it is not intended that the invention be limited in respect to the particular liquid selected for encapsulation.

The microcapsules used in the present invention may be of any composition and be prepared using any known method, provided that the device and method of the present invention function substantially as described herein. Examples of systems that are suitable for use in preparing microcapsules for use in the present invention include melamine-formaldehyde, urea-formaldehyde, and polyurea encapsulation systems.

When microcapsules are combined with the previously described non-film-forming microparticulate adhesive, it is advantageous that the ratio of microcapsules to adhesive microparticles ranges from about 1:5 to about 4:1, preferably from about 1:2 to about 2:1, and most preferably from about 1:1 to about 2:3. Moreover, and advantageously, the microparticles may have an average diameter of about 10 µm to about 90 µm. Preferably, the microparticles may have an average diameter of about 20 µm to about 60 µm and the microcapsules an average diameter of about 15 µm to about 40 µm.

The surfaces upon which the adhesive composition is applied may consist of any number of materials, e.g., polymeric film, foil, fabric or paper. Each surface may be of the same, or different, material.

The present invention also provides a method for a person to obtain repeated, but selective, exposure of a microencapsulated liquid. That method comprises (a) providing two surfaces adhered to each other by an adhesive composition, the adhesive composition comprising a non-film forming adhesive comprising a plurality of adhesive polymeric microparticles and microcapsules of an average diameter of about 5 µm to about 60 µm which have the liquid therein, wherein at least a portion of the microcapsules are broken when the surfaces are separated, and wherein the adhesive has the ability to readhere the surfaces to each other after the surfaces are separated and microcapsules broken, (b) separating the two surfaces to break the at least a portion of the microcapsules, and (c) contacting the two surfaces to readhere the two surfaces to each other. The components used in the foregoing method were previously described in connection with the inventive device.

The method further provides for the repetition of steps (b) and (c) at least once, thereby allowing one the capability of selectively re-sampling the liquid.

The preparation of devices of the present invention, e.g., fragrance samplers, may be undertaken by any known method, such methods being well known to those skilled in the art.

The following examples further illustrate the present invention but, of course, should not be construed as in any way limiting its scope.

EXAMPLES

The following three comparative examples demonstrate the performance of a conventional fragrance sampler prepared using a film-forming adhesive.

Comparative Example A

A slurry was prepared by mixing the following components:

| Component | Parts (by weight) |
|---|---|
| Microcapsules[1] | 20 |
| Water | 58 |
| Polyvinyl alcohol[2] | 12 |
| Thickener | 10 |
| Total | 100 |

[1]Microcapsules containing a fragrance used in this composition were prepared using the urea-formaldehyde encapsulation method.
[2]Fully hydrolyzed polyvinyl alcohol was used as the film-forming adhesive.

The slurry was mechanically coated on fragrance grade paper at a coating weight of about 5 to 11 $g/m^2$. The coated sheet was then folded and dried, forming a conventional fragrance sampler.

Upon opening, microcapsules were broken, and fragrance was released. However, the sampler was unable to be effectively re-sealed.

Comparative Example B

The methodology set forth in Comparative Example A was repeated, except that the microcapsules used in the slurry consisted only of those prepared using the melamine-formaldehyde encapsulation method.

As was the case in respect to the sampler prepared in Comparative Example A, microcapsules were broken, and fragrance was released, when the sampler was opened. The sampler, however, was unable to be effectively re-sealed.

Comparative Example C

The methodology set forth in Comparative Example A was repeated, except that the microcapsules used in the slurry consisted only of those prepared using the polyurea encapsulation method.

As was the case in respect to the sampler prepared in Comparative Examples A and B, microcapsules were broken, and fragrance was released, when the sampler was opened. The sampler, however, was unable to be effectively re-sealed.

The following three examples demonstrate the performance of fragrance samplers prepared using a non-film-forming adhesive in accordance with the present invention.

Example 1

A slurry was prepared by mixing the following components:

| Component | Parts (by weight) |
|---|---|
| Microcapsules[1] | 17 |
| Water | 13 |
| Morstic 240[2] | 65 |
| Thickener[3] | 5 |
| Total | 100 |

[1]Microcapsules containing a fragrance used in this composition were prepared using the urea-formaldehyde encapsulation method.
[2]This acrylic, non-film-forming, water-based repositionable microparticle adhesive (30% solids) is available from Morton International.
[3]The same thickener used in the Comparative Examples was used in this example.

A fragrance sampler was prepared in the same manner as in the Comparative Examples, but with the composition described above, which included a non-film-forming, microparticle adhesive. Upon opening, microcapsules were broken, and fragrance was released. Moreover, the sampler was able to be re-sealed and opened several times. Further, each time the sampler was opened, an amount of fragrant oil was released into the air.

Example 2

The methodology set forth in Example 1 was repeated, except that the microcapsules used in the slurry consisted only of those prepared using the melamine-formaldehyde encapsulation method.

As was the case in respect to the sampler prepared in Example 1, when the sampler was opened, microcapsules were broken, and fragrance was released. Moreover, the sampler was able to be re-sealed and opened several times. Further, each time the sampler was opened, an amount of fragrant oil was released into the air.

Example 3

The methodology set forth in Example 1 was repeated, except that the microcapsules used in the slurry consisted only of those prepared using the polyurea encapsulation method.

As was the case in respect to the samplers prepared in Examples 1 and 2, when the sampler was opened, microcapsules were broken, and fragrance was released. Moreover, the sampler was able to be re-sealed and opened several times. Further, each time the sampler was opened, an amount of fragrant oil was released into the air.

All of the references cited herein are hereby incorporated in their entireties by reference.

While this invention has been described with an emphasis upon a preferred embodiment, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A reusable device for exposing a microencapsulated liquid comprising two surfaces adhered to each other by an adhesive composition, the adhesive composition comprising a non-film forming repositionable adhesive comprising a plurality of adhesive polymeric acrylic microparticles having an average diameter of about 10 μm to about 90 μm and microcapsules of an average diameter of about 5 μm to about 60 μm which have the microencapsulated liquid therein and which are adhered to each surface by the adhesive, wherein at least a portion of the microcapsules are broken when the surfaces are separated, and wherein the adhesive has the ability to readhere the surfaces to each other after the surfaces are separated and microcapsules broken.

2. The device according to claim 1, wherein the microcapsules are prepared using a melamine-formaldehyde encapsulation system, a urea-formaldehyde encapsulation system, or a polyurea encapsulation system.

3. The device according to claim 1, wherein the ratio of microcapsules to adhesive microparticles ranges from about 1:5 to about 4:1.

4. The device according to claim 1, wherein the adhesive is at least one alkyl acrylate polymer.

5. The device according to claim 4, wherein the alkyl group of each alkyl acrylate polymer contains from 4–16 carbon atoms.

6. The device according to claim 5, wherein the alkyl group of each alkyl acrylate polymer contains from 8–12 carbon atoms.

7. The device according to claim 6, wherein the adhesive is selected from the group consisting of poly(isooctyl acrylate), poly(2-ethylhexyl acrylate), and mixtures thereof.

8. The device according to claim 7, wherein the adhesive microparticles have an average diameter of about 20 μm to about 60 μm.

9. The device according to claim 5, wherein the microcapsules have an average diameter of about 15 μm to about 40 μm.

10. The device according to claim 1, wherein the adhesive is at least one alkyl acrylate polymer, the adhesive microparticles have an average diameter of about 10 μm to about 90 μm, and the ratio of microcapsules to adhesive microparticles ranges from about 1:2 to about 2:1.

11. The device according to claim 10, wherein the alkyl group of each alkyl acrylate polymer contains from 8–12 carbon atoms.

12. The device according to claim 11, wherein the microcapsules are prepared using a melamine-formaldehyde encapsulation system, a urea-formaldehyde encapsulation system, or a polyurea encapsulation system.

13. The device according to claim 1, wherein the microencapsulated liquid comprises a fragrant oil.

* * * * *